United States Patent
Eyal et al.

(10) Patent No.: US 6,172,242 B1
(45) Date of Patent: *Jan. 9, 2001

(54) PROCESS FOR THE PRODUCTION OF ERYTHORBIC ACID

(75) Inventors: Aharon Meir Eyal; Asher Vitner; Tal Reuveni; Betty Hazan, all of Jerusalem (IL)

(73) Assignee: Yissum Research Development Company of the Hebrew University of Jerusalem, Jerusalem (IL)

( * ) Notice: Under 35 U.S.C. 154(b), the term of this patent shall be extended for 0 days.

This patent is subject to a terminal disclaimer.

(21) Appl. No.: 09/296,913

(22) Filed: Apr. 22, 1999

Related U.S. Application Data

(63) Continuation of application No. 08/979,384, filed on Nov. 26, 1997, now abandoned, and a continuation-in-part of application No. 08/952,491, filed on May 31, 1996, now Pat. No. 6,037,480.

(30) Foreign Application Priority Data

Dec. 1, 1996 (IL) .......................................... 119730

(51) Int. Cl.$^7$ ................................................ C07D 307/62
(52) U.S. Cl. ............................ 549/315; 252/364; 435/126
(58) Field of Search ............................ 549/315; 252/364; 435/126

(56) References Cited

U.S. PATENT DOCUMENTS 2,160,621  5/1939  Ohle ...................................... 260/344

(List continued on next page.)

FOREIGN PATENT DOCUMENTS

0133493 A2  2/1985  (EP) .
1 426 018   2/1976  (GB) .
40-2531     2/1965  (JP) .
WO96/38433  12/1996 (WO) .
WO98/24777  6/1998  (WO) .

OTHER PUBLICATIONS

Kirk–Othmer, *Encyclopedia of Chemical Technology*, 4$^{th}$ Ed., vol. 6, p. 364.

Wennersten, "The Extraction of Citric Acid from Fermentation Broth Using a Solution of a Tertiary Amine," *J. Chem. Tech. Biotechnol.*, No. 33B, pp. 85–94 (1983).

Eyal et al., "Recovery and Concentration of Strong Mineral Acids from Dilute Solutions Through LLX," *Solvent Extraction and Ion Exchange* 9:195–210 (1991).

Bauer et al., "Reactive Extraction of Citric Acid from an Aqueous Fermentation Broth," *Ber. Bunsenges. Phys. Chem.* 93:980–984 (1989).

* cited by examiner

Primary Examiner—Elli Peselev
(74) Attorney, Agent, or Firm—Williams, Morgan & Amerson, P.C.

(57) ABSTRACT

The invention provides a process for the recovery of erythorbic acid from an aqueous feed solution containing values of erythorbic acid at a concentration of less than 0.7 mol/kg, comprising extracting said erythorbic acid with a water-immiscible organic extractant composition comprising at least one secondary or tertiary alkyl amine in which the aggregate number of carbon atoms is at least 20, as a primary extractant, and a polar extraction enhancer compound; wherein said extractant composition comprises at least 2 moles of said polar extraction enhancer compound per one mole of primary extractant; separating said erythorbic acid-containing organic extractant composition from residual aqueous solution, and subjecting said erythorbic acid-containing organic extractant composition to a stripping operation with aqueous solution at a temperature of at least 20° C. higher than the temperature at which said extraction is carried out; whereby there is obtained an aqueous solution of erythorbic acid in which the concentration of erythorbic acid is higher than its concentration in said aqueous feed solution.

27 Claims, 2 Drawing Sheets

U.S. PATENT DOCUMENTS

| | | | |
|---|---|---|---|
| 2,443,487 | 6/1948 | Wenner | 260/344.5 |
| 4,275,234 | 6/1981 | Baniel et al. | 562/584 |
| 4,994,609 | 2/1991 | Baniel et al. | 562/580 |
| 5,041,563 | 8/1991 | Fahrni et al. | 549/315 |
| 6,037,480 * | 3/2000 | Eyal et al. | 549/315 |

PROCESS FOR THE PRODUCTION OF ERYTHORBIC ACID

This application is a continuation of U.S. Ser. No. 08/979,384, filed on Nov. 26, 1997, now abandoned and is also a continuation-in-part of U.S. Ser. No. 08/952,491, filed on May 31, 1996, now U.S. Pat. No. 6,037,480.

The present invention relates to a process for the production of erythorbic acid. More particularly, the present invention relates to the recovery of erythorbic acid from aqueous solutions containing values of erythorbic acid in low concentrations, the term values of erythorbic acid as used herein referring to erythorbic acid, salts thereof, derivatives thereof and mixtures thereof.

Erythorbic acid is an isomer of ascorbic acid and is also named isoascorbic acid and D-araboascorbic acid. This acid and its salts (erythorbates) are widely used as alternatives to ascorbic acid and its salts in non-Vitamin C products. Erythorbates traditionally have two functions. First they act as antioxidants, controlling color and flavor deterioration in many foods, and as antimicrobial agents for foods. Secondly, erythorbates are used as meat-curing accelerators, speeding and controlling the nitrite-curing reaction, while prolonging color and shelf-life. Erythorbates therefore have many uses in the food industry and are used in conjunction with such comestibles as meat, fish, poultry, beverages, fruits and vegetables.

Takeshi Takahashi's U.S. Pat. No. 3,052,609 assigned to Sankyo Co., teaches a process for the production of D-araboascorbic acid which comprises subjecting one or more substances selected from the group consisting of D-glucose, D-gluconic acid, D-glucono-y-lactone, D-glucono-8-lactone, sucrose, maltose and starch to the action of an enzyme of a microorganism selected from the group consisting of *Penicillium decumbens, Penicillium chrysogenum, Penicillium chrysogenum* mut. *fulvescens* Takashima, Arima and Abe, *Penicillium meleagrinum, Penicillium cyaneofulvum* and *Penicillium notatum* in the presence of oxygen and recovering the D-araboascorbic acid which is formed.

In carrying out the process according to that invention, both a direct fermentation method and a cell suspension process may be applied.

In carrying out the direct fermentation method, too low concentration of the carbon source would result in decreased conversion to the product due to consumption of the source for the propagation of the cells. Too high concentrations would lead to lower yield due to greater conversion to by-products and to a larger amount of residual sugar. It is preferable to use a concentration between 0.5 and 10%. It is also preferred to keep the concentration between about 0.5 and 1.0% by continuously adding the material. Other substances present in the medium are organic or inorganic assimilable nitrogen sources, mineral salts and a trace of various metals. pH is usually maintained between about 3 and 7. The time required for the fermentation is from 5 to 10 days in the case of surface culture and from 3 to 7 days in the case of submerged culture. The preferred temperature in the fermentation is 26 to 28° C.

Production of D-araboascorbic acid using the intact cell or dried cell preparation is effected in a buffer solution having a pH of about 4.0 to 6.0. The concentration of the carbon source is 0.5 to 10%, the temperature between 35 and 30° C. and the time is between 50 to 80 hours. The substrate is preferably added in intervals to keep its concentration between 0.5 and 1.0%.

The isolation of D-araboascorbic acid may be performed by first removing the mycelium by means of filtration or by means of a centrifugal procedure and subsequently applying the known procedures for isolating L-araboascorbic acid to the filtrate or supernatant. For example, an adequate amount of barium acetate is added to remove phosphates and sulfates and organic impurities are removed by treatment with active charcoal, followed by adsorption of the desired product on anion-exchange resin such as Amberlite IR-4B and elution with aqueous hydrochloric acid. Furthermore, impurities are removed by means of a small amount of active charcoal and butanol and D-araboascorbic acid is crystallized by concentration in vacuum at low temperature under carbon dioxide, followed by recrystallization from solvent such as acetone or ethanolligroin.

The product concentrations, g/l, (and fermentation pH and duration) in Examples 1 to 7 of said U.S. patent are respectively: 0.5–1.2 (pH=5–6, 7 days), 2–3 (pH=5, 3 days), 4.2 (pH=5.6, 4 days), 5.3 (pH=5.3, 5 days), 5 (pH=5.6, 10 days), 1.4 (pH=5, 4 days), 10.3 (5.0 for the initial 20 hours and about 4.0 for the remaining 40 hours).

In Examples 1 to 6 the culture filtrate, after treatment with 1 g. of barium acetate and 0.1 g. of active charcoal, is adsorbed on ion-exchange resin IR-4B, followed by elution with 1 liter of 1 N-HCl. About 70% of the total content of the desired product is eluted in fractions in volume of 200–300 ml. after initiation of the elution. These fractions are shaken with butanol and, after addition of a small amount of active charcoal, are filtered to give an almost colorless transparent liquor, which is concentrated to near dryness in vacuum at temperature below 30° C. under $CO_2$, followed by several concentrations in the presence of ethanol to remove most of the water. The oily substance thus obtained is allowed to stand in a vacuum desiccator for 2–3 days to separate crystalline D-araboascorbic acid.

In Examples 7 and 8, after completion of the reaction, pH is adjusted to 2.0 with $H_2SO_4$ and the mycelium is separated by filtration. The filtrate is treated with about 1 g. of barium acetate and about 0.1 g. of active charcoal per liter followed by filtration. The filtrate is passed through ion-exchange resin IR-4B pretreated with acetic acid to adsorb D-araboascorbic acid contained in the filtrate. The ion-exchange resin column is treated with 1 N-HCl and about 70% of the total content is eluted in 200–300 ml. of the first fractions from the elution. The eluate, after addition of a small amount of active charcoal, is filtered to give almost colorless transparent solution. The solution is concentrated to near dryness in vacuum under $CO_2$. Repeated concentrations after addition of ethanol to the residue give an oily substance almost water free. The oily substance thus obtained is concentrated in vacuum to give crystalline D-araboascorbic acid.

The recovery yield shown in examples 3 to 8 were low, 19, 23, 20, 29, 29 and 28%, respectively. A possible explanation for that is the presence of HCl in the eluate. On concentration of the latter, HCl could cause decomposition of the product. Another disadvantage of the recovery process is the high consumption of acids and bases and the resulting formation of by-product salts.

Seven years after said U.S. patent was granted, the inventor issued an article entitled: Erythorbic acid fermentation, which was published in Biotechnology and Bioengineering Vol. XI, pages 1157–1171 (1969). (Takahashi had several earlier publications, see references in the 1969 article.) Two other related publications, by Yagi and co-workers and by Shimizu and co-workers, respectively are: Studies on Erythorbic acid production by fermentation, Part I, Erythorbic acid producing strain and cultural conditions and Part II, Erythorbic acid production by jar fermentors, published in Agr. Biol. Chem. Vol. 31, pages 340–345 and 346–352, respectively (1967). These articles describe studies directed to development of an industrial process including strain improvement, optimization of culture solution (carbon source, nitrogen source, additives, effects of iron and copper and of chelating agents), temperature, aeration and agitation.

Glucose and sucrose were found to be the most appropriate carbon source. Glucose concentration should be in the range of 8–12%. In one test the fermentation was started with 8% glucose, 8% glucose was fed on the third day and 4% glucose was fed on the sixth day. The yield in that case amounted to about 40% of the total glucose supplied. The erythorbic acid concentration in the solution reached 80 g/l. The preferred temperature is about 30° C.

In the course of typical fermentations the pH of the broth is gradually lowered along the consumption of sugar and remains in the range of 3.8–4.5. Erythorbic acid production reaches maximum yield at 5–7 days.

Working with washed cells at lower glucose concentrations show higher yields. In a test comparing fermentations starting with 1, 2 and 3% glucose (at 29° C.), the following yields were found after 48 hours: about 80, 65 and 38% respectively. The initial pH was 5, decreasing to 4.0–4.3 at the end.

The broth was clarified by separation of the mycelia, and by successive filtration after addition of $Ba(OH)_2$ and treated with active carbon and a strong acid cation exchanger, Duolite C-20 in acid form. Then it was treated with a weak base anion exchanger, Amberlite IR-45, in free base or acetate form, which adsorbed the erythorbic acid. The resin was then washed with water and eluted with 1N HCl solution. Erythorbic acid was crystallized by concentration of the eluate in vacuum. The total yield of erythorbic acid recovery was 60%, probably due to decomposition during the concentration, which decomposition is facilitated by the HCl present.

In order to decrease this decomposition problem the selectivity of the anion exchanger was used for separation between the eluting HCl and the eluted erythorbic acid. A continuous extraction with a multi-bed resin system was used. Amberlite IR-4B was found to be the most suitable weak base anion exchanger for that purpose. The eluant was 1NHCl and the regenerant was 2N NaOH solution. Using that system, recovery of 90.9% of crude crystals and 4.5% in a mother liquor were found. On recycle of HCl+ erythorbic acid containing solutions to the resin and on recystallization of the HCl free erythorbic acid solutions, a yield of 91.2% on the crude erythorbic acid content of the broth was achieved out of which 68.4% were in free acid form and 22.8% in sodium salt form.

The method of separation described consumes acids and bases and forms salts (NaCl in this particular case), as an undesired by-product. In the fermentation liquor the erythrobic is a mixture of the free acid form and a salt, depending on the final pH. Addition of $Ba(OH)_2$ according to the procedure suggested here, converts more of it into the salt form (using a barium salt instead of the base would avoid neutralization of free erythorbic acid, but would contaminate the solution with an anion of another acid). In the next stage all the erythorbate salt present in the solution is converted to the free acid form on a strong acid cation exchanger. More than one mole of a strong acid per mole of acidulated erythorbate are consumed for the regeneration of the cation exchanger. The erythorbic acid (free) containing solution is contacted with a weak base anion exchanger on which the acid is bound. On the elution of the adsorbed erythorbic acid more than one mole of HCl is adsorbed on the anion exchanger per mole of eluted erythorbic acid. Then at least one mole of base per mole of adsorbed HCl is used for the regeneration of the anion exchanger.

The recovery process described in the prior art thus suffers from several disadvantages. In order to separate erythorbic acid from the relatively dilute fermentation liquor at a reasonable concentration, it uses the chemical energy of the (indirect) neutralization of a mineral acid and mineral base (HCl and NaOH in the examples given above). As a result, costly reagents are consumed and an undesired salt is formed and there arises a need to dispose thereof, in addition, anions present in the fermentation liquor, mainly phosphate, are removed in a pretreatment, which could introduce traces of barium to the product and form barium salts which also require disposal. Cations present in the fermentation liquor are removed by strong acid cation exchangers, which also add to the salt production.

Thus, despite the widely felt need for a more attractive process to meet the exceedingly high demand for erythorbic acid, to date no such process has been proposed or commercialized.

In 1976, there issued British Patent 1,426,018 and in 1981 there issued the corresponding U.S. Pat. No. 4,275,234, directed to the recovery of acids from aqueous solutions. In said patents, there are exemplified the recovery of citric acid, lactic acid, oxalic acid, and phosphoric acid from an aqueous solution of the same acid; in fact, said U.S. patent is specifically limited in its claims to the recovery of one of said four acids.

While the process of the present invention as defined herein formally falls within the scope of said aforementioned British patent, the relevant teachings of which are incorporated herein by reference, and in this sense constitutes a selection therefrom, as will be explained further below, not only do said patents neither teach, suggest, nor exemplify the applicability of said process to the recovery of erythorbic acid, but in fact, from a careful analysis of said patents, one would not expect said process to be feasible for the recovery of erythorbic acid, as is also evidenced by the fact that twenty years have passed from the publication of said British patent without any person skilled in the art either suggesting or applying said process to erythorbic acid recovery.

Referring now to said patents and the teachings thereof, one finds that the process taught therein utilizes the effect of temperature on phosphoric and carboxylic acid extraction by amine-based extractants. The term "amine" as used herein means water-immiscible amine, with a total of at least 20 carbon atoms on its chains. Said patents teach that such amine-based extractants (ABE) lose much of their extraction efficiency upon temperature elevation. This loss of efficiency is referred to as "temperature sensitivity of extraction" (TS). The magnitude of this TS can be represented by the ratio of the distribution coefficient at the lower temperature ($D_{T1}$) and to the distribution coefficient at the higher temperature ($D_{T2}$). High TS provides for the purification and the concentration of carboxylic acids through altering the temperature between extraction and back-extraction or stripping. The acid is extracted from the fermentation liquor by an ABE at low temperature, and is then back-extracted with water at an elevated temperature. The aqueous solution obtained from that back-extraction is, in many cases, more concentrated than in the fermentation liquor. This process is referred to herein as the "temperature swing process" (TSP). The attraction of such processes is in the fact that the sole energy consumption is that of sensible heat, which saves a lot of the latent heat of water evaporation in the final concentration.

As explained in U.S. Pat. No. 4,275,234:

"The concepts of "lower temperature" and "higher temperature" are not understood in absolute terms. What matters is the temperature differential. This will have to be at least 20 degrees (centigrade), both for operation convenience and in order to make both the extraction and the back-extraction as complete as possible. The extraction may be carried out at temperatures as low as near the freezing point of the aqueous acid solution and the temperature of the back-extraction may be at or near the boiling point of the extract or the water at atmospheric pressure, or if the back-extraction is carried out under elevated pressure, at an even higher temperature, always on condition that the temperature and pressure are so chosen that the amine remains in the organic phase. In many cases the extraction can be carried out at or near room temperature, and the stripping operation at a temperature of about 20 to 40 degrees (Centigrade) above room temperature. As a rule, the stripping operation is the more effective, the higher the stripping temperature, but the extraction and stripping temperatures will be selected in individual cases in accordance with practical factors, such as corrosion-resistance and the costs of the equipment, costs of heating and cooling of the streams of the acid solution, the extract and the extractant, the required concentration of stripped acid, etc.

"If the aqueous liquid used for stripping the extract is water, the back-extract is an aqueous solution of the free acid. If desired, the back-extracting operation may be so conducted that the back-extract is an aqueous solution of a salt of the extracted acid. For example, back-extraction with an aqueous alkali metal (in this context "alkali metal" includes ammonium) hydroxide solution yields an aqueous solution of the corresponding alkali metal salt of the extracted acid. Or the aqueous back-extracting liquid may be, for example, an alkali metal chloride solution. In this case, too, the back-extract contains the corresponding alkali metal salt of the extracted acid while the amine in the extractant is converted into its hydrochloride. This will thus have to be decomposed, e.g. by treatment with calcium hydroxide, for reconstituting the extractant. Sometimes it is advantageous to perform first a back-extraction with water in order to recover the major part of the acid in the free state. The residue of acid remaining in the solvent extract can then be back-extracted with an alkali metal hydroxide or salt solution.

"The most favorable selection of the temperature of the extracting operation and of the compositions of the extractant, as regards both the amine and the solvent, will also be determined according to the given condition of particular cases, e.g., the kind of acid, its concentration in the original aqueous solution, the impurities present in that solution. The major aim in both the extracting and stripping operations will be to achieve as favorable a distribution coefficent as possible for the distribution of the acid between the aqueous and organic phases. In the extraction operation, this has to be in favor of the extractant; in the stripping operation, in favor of the aqueous phase."

As stated above, the characterizing feature of said patents is that back-extraction is performed at a temperature higher than that of the extraction. For certain acids, there is shown efficient extraction at about room temperature. Back-extraction at about 100° C. provides for a back extract, the concentration of which is similar to, or even higher than, that of the feed. In fact, a major part of citric acid production in the world is based on this process, using tridodecyl amine as the primary extractant and 1-octanol as the enhancer [Kirk-Othmer, *Encyclopedia of Chemical Technology*, 4th Ed., Vol. 6, p. 364].

The degree of product concentration in the TSP (the uphill pumping effect) depends strongly on the magnitude of the TS. The thermodynamic explanation for the TS is not clear enough. One could suggest that as the extraction process is exothermic, equilibrium is shifted backwards on temperature elevation. That would, however, be too simplistic. Thus, the most exothermic extraction is that of strong mineral acids, but no TS is found for their extraction by straight chain amines. To the best of our knowledge, this complex phenomenon was not fully explained in said patents, and no tools were provided for predicting the magnitude of TS from the structure of the extracted acid.

The magnitude of the TS for extraction of various carboxylic acids by an extractant composed of 0.5 mol/kg trilauryl amine also named tridodecyl amine (Henkels Alamine 304) and 10% octanol in a kerosenic diluent have now been tested. The results are presented below in Table 1:

TABLE 1

| | | TS in Equilibrium with Aqueous Solutions of (mol/kg) | | | |
|---|---|---|---|---|---|
| Acid | pKa | 0.05 | 0.2 | 0.3 | 0.475 |
| Maleic[2] | 1.93 | 1.1 | 1.0 | 1.0 | 1.0 |
| Oxoglutaric[2] | 2.57 | 2.4 | 1.5 | 1.3 | 1.1 |
| Malonic[2] | 2.83 | 3.6 | 1.5 | 1.3 | 1.1 |
| Tartaric[2] | 3.01 | 3.4 | 3.2 | 2.7 | 2.4 |
| Citric[3] | 3.13 | 6.0 | 3.1 | 2.6 | 2.2 |
| Malic[2] | 3.22 | 4.0 | 4.3 | 4.0 | 4.0 |
| Gluconic[2] | 3.75 | 2.1 | 2.3 | 2.4 | 2.6 |
| Lactic[1] | 3.86 | 2.5 | 2.4 | 2.4 | 2.2 |
| Succinic[2] | 4.2 | 4.3 | 4.0 | 4.0 | 4.1 |
| Glutaric[2] | 4.4 | 3.9 | 4.5 | 4.5 | 4.4 |
| Acetic[1] | 4.76 | 2.3 | 2.4 | 2.4 | 2.4 |
| Butyric[1] | 4.81 | 2.1 | 2.0 | 2.0 | 1.8 |
| Isobutyric[1] | 4.84 | 1.9 | 1.5 | 1.4 | 1.1 |
| Propionic[1] | 4.87 | 1.7 | 1.5 | 1.3 | 1.1 |

The temperature sensitivity of carboxylic acid extraction by 0.5 mol/kg Alamine 304 + 10% octanol in kerosene.
The temperature sensitivity (TS) is presented as the distribution coefficient at 30° C., divided by that at 75° C., at various equilibrium aqueous phase concentrations.
[1]Monocarboxylic acid
[2]Dicarboxylic acid
[3]Tricarboxylic acid One can see that the TS may depend on the equilibrium concentration of the acid in the aqueous phase and that it varies significantly from one acid to the other. No linear correlation is found, however, between the TS and the strength of the acid or another defined characteristic thereof. The strongest TS was found for citric acid at the low concentration of 0.05 mol/kg; some dicarboxylic acids show a higher TS than their monocarboxylic analogues. That might indicate a tendency of TS to increase with an increase in the number of carboxylic groups. Isolating this parameter from the others is difficult.

Extraction of strong mineral acids by ABE is very efficient, reaching stoichiometric levels already at equilibrium with dilute aqueous solutions. That is true even for the weakest straight chain aliphatic amines, the tertiary ones reaching the stoichiometric extraction of 1 mol of HCl per mol of amine in equilibrium with aqueous solutions of about 0.5%. High efficiency is also found in extracting strong carboxylic acids having a pKa less than 2.5. The efficiency is, however, much lower on extracting weaker carboxylic acids by tertiary amines in a kerosenic diluent. Said low efficiency is particularly pronounced in the low concentration range. In order to avoid low yields of extraction, extraction enhancers are introduced into the extractant.

It is well-known that polar and protic compounds provide for enhancement of acid extraction by amines. These compounds may act as acid extractants by themselves, but are much weaker extractants than the amines. Extractants comprising amines and enhancers show synergistic effects in most cases, i.e., acid extraction by such extractants is much higher than the added contribution of the components.

In the description of the invention herein, and to avoid confusion, the term "primary extractant" will be used for long-chain amines used for extractions, and the term "enhancer" will be used for polar and protic extractant components, the extraction power of which is smaller than that of the primary extractant. Suitable enhancers are polar, and preferably protic compounds, including alkanols, ketones, aldehydes, esters and ethers of various molecular weights.

Desired extractants should provide high efficiency in extraction (relatively low extractant volumes, a small number of extractant stages and high yields), high selectivity, low water miscibility, low toxicity (particularly for food grade products), and efficient stripping of the extracted acid from the extract. The acid can be removed from the extract through interaction with an aqueous solution of a base to form its salt. In most cases, however, the acid is the required product rather than the salt, and acid recovery from the extract is performed by back-extraction with water or by distillation, where feasible.

As is known, high efficiency in extraction from the feed and high efficiency in stripping are conflicting requirements. Back-extraction of the extracted acid from a strong extractant requires high volumes of water and results in a very dilute aqueous solution of the acid (back-extract). The high cost of product concentration may make the whole process impractical. Distillation from a strong extractant requires high temperatures and may result in the decomposition of the acid and/or the extractant.

Extraction enhancers are polar and, preferably, protic compounds that have very low extraction capacity on their own, but significantly improve the extraction efficiency of ABE. The enhancement is explained by stabilization through solvation of the amine-acid ion pair. Octanol is used as an enhancer in the industrial TSP for production of citric acid.

Extraction enhancers have, however, an adverse effect on TSP, as the temperature sensitivity decreases with an increase in enhancer content. Such an effect is shown below in Table 2:

TABLE 2

| Amine | Octanol | D30/D75 at Aqueous Concentration | | |
|---|---|---|---|---|
| mol/kg | mol/kg | 0.02 | 0.5 | 1.5 |
| 0.2 | 0.31 | 30.0 | 6.4 | 2.1 |
| 0.2 | 0.62 | 10.8 | 2.0 | 1.3 |
| 0.2 | 2.0 | 4.9 | 1.3 | 1.1 |
| 0.5 | 0.31 | 31.3 | 3.7 | 1.4 |
| 0.5 | 0.62 | 4.6 | 1.5 | 1.1 |
| 0.5 | 2.0 | 2.1 | 1.1 | 1.05 |
| 1.0 | 0.31 | 10.5 | 1.2 | 1.07 |

TABLE 2-continued

| Amine | Octanol | D30/D75 at Aqueous Concentration | | |
|---|---|---|---|---|
| mol/kg | mol/kg | 0.02 | 0.5 | 1.5 |
| 1.0 | 0.62 | 4.9 | 1.1 | 1.01 |
| 1.0 | 2.0 | 1.8 | 1.08 | 1.03 |

The dependence of the temperature sensitivity of citric acid extraction by amine-based extractant on amine concentration, enhancer (octanol) concentration, and on equilibrium aqueous phase concentration. The temperature sensitivity is presented as the ratio of distribution coefficient at 30° C. and 75° C.).

There is, therefore, a trade-off between extraction efficiency and the magnitude of the TS. Thus, aiming at a higher degree of product concentration in the process leads to lower efficiency, particularly at the low concentration end, resulting in lower recovery yields, i.e., higher product losses. The absolute losses, expressed, for example, by the product concentration in the raffinate, depend on the shape of the distribution curve at the low concentration end. The proportional loss is mainly determined by the concentration of the acid in the fermentation liquor.

The TSP was implemented for citric acid recovery from fermentation liquors due to the unique, favorable combination of very high temperature sensitivity (the highest reported so far) and the relatively very high concentration of citric acid in the fermentation liquor, typically 16–18%. Even at these unique conditions, the enhancer level should be reduced to a minimum. R. Wennerstem [*J. Chem. Tech. Biotec.*, No. 33B, pp. 85–94 (1983)] studied the effect of the various extractant parameters and concluded that hydrocarbons are the preferred diluents, as polar diluents reduce the temperature effect. Cooling below ambient temperature or preconcentration of the fermentation liquor [U.S. Pat. No. 4,994,609] are required to avoid major product losses.

The above limitations brought Bauer, et al. to conclude, in 1989, that a TSP is not even economic for citric acid, and that displacement of the extracted acid by another acid (acetic) is preferable [Bauer, et al., *Ber. Bunsenges. Phys. Chem.*, Vol. 93, pp. 980–984 (1989)].

It is important to note at this juncture that erythorbic acid does not carry a carboxyl group and therefore it is not a carboxylic acid, nor is it a mineral acid. Consequently, patents and disclosures which are directed to processes for treating or recovering carboxylic and/or mineral acids do not include erythorbic acid within their scope.

According to its pKa, erythorbic acid is quite weak, being more than an order of magnitude weaker than citric acid. Its low acidity and high hydrophilicity (since it carries 4 hydroxyl groups) reduce its extraction efficiency.

Extraction efficiency is determined by the distribution coefficient dependence on the aqueous phase concentration (the shape of the distribution curve). The distribution coefficient at the high concentration end determines the maximal loading of the extractant, and thereby, the volume of the recycled extractant. The distribution coefficient at the low concentration end determines the ability to approach complete extraction, and thereby, the extraction yield. For extraction of a component from a dilute feed, the yield of extraction is very important. Reaching high yields in extracting from a dilute feed a relatively weak and highly hydrophilic acid, such as erythorbic acid, would require high enhancer levels.

Test results in Table 1 above show that the strongest temperature sensitivity so far is found for citric acid, and that this temperature sensitivity drops with a decreasing number of carboxyl groups. Nothing in these results, or in those found in the literature, indicates that erythorbic acid would show a higher temperature sensitivity than citric acid.

Even if erythorbic acid extraction had the temperature sensitivity of citric acid extraction, one would not consider its recovery from dilute solutions in the TSP, due to the fact that at low enhancer levels, the losses would be extremely high. On the other hand, at high enhancer levels, the temperature sensitivity decreases. Thus, the major advantage of the process, i.e., recovering the product at a concentration substantially higher than that of the fermentation liquor, would be lost.

In light of the above, it was extremely surprising to discover that the temperature sensitivity of erythorbic acid extraction by amine-based extractants is very high and is maintained, even at high enhancer levels. Based on this discovery, there is now provided, according to the present invention, a process for the recovery of erythorbic acid from an aqueous feed solution containing values of erythorbic acid at a concentration of less than 0.7 mol/kg, comprising extracting said erythorbic acid with a water-immiscible organic extractant composition comprising (a) at least one secondary or tertiary alkyl amine in which the aggregate number of carbon atoms is at least 20, as a primary extractant, and (b) a polar extraction enhancer compound; wherein said extractant composition comprises at least 2 moles of said polar extraction enhancer compound per one mole of primary extractant; separating said erythorbic acid-containing organic extractant composition from residual aqueous solution, and subjecting said erythorbic acid-containing organic extractant composition to a stripping operation with aqueous solution at a temperature of at least 20° C. higher than the temperature at which said extraction is carried out; whereby there is obtained an aqueous solution of erythorbic acid in which the concentration of erythorbic acid is higher than its concentration in said aqueous feed solution.

The process of the present invention is so effective that in preferred embodiments thereof as described hereinafter, said erythorbic acid can be recovered from an aqueous feed solution containing said acid at a concentration of less than 0.5 mol/kg.

Extractants comprising relatively strong amines as the primary extractant, show nearly no temperature sensitivity on the efficiency of extracting strong mineral acids. It was, however, found that relatively weak amines do show such effect. An example of such weak amines is the sterically-hindered, branched chain amines with branching on a carbon close to the nitrogen atom [Eyal, et. al., *Solvent Extraction and Ion Exchange,* Vol. 9, pp. 195–236 (1991)]. These amines are weaker by more than two orders of magnitude than straight chain amines, and weaker than branched chain amines with branching far from the nitrogen atom. Such amines are too weak to extract most weak acids and are not suitable for use as primary extractants in the present invention. For simplicity of language, the term "branched chain amines" will be used here just for sterically hindered, relatively weak amines with branching close to the nitrogen atom.

Branched chain amines are too weak to extract many of the carboxylic acids, particularly hydroxycarboxylic acids. Straight chain amines are much more efficient, but complete extraction without resorting to high cooling costs requires the use of extraction enhancer. This is particularly true for extraction from dilute feed solutions. Yet, the stronger is the enhancer and the higher its contents, the lower is the sensitivity of extraction efficiency to temperature. Thus, amine-based extractants, comprising relatively strong enhancers at high proportions of enhancers, show high efficiency in extraction, but lose most of the advantage in back-extraction at higher temperature, according to U.S. Pat. No. 4,275,234.

According to the known practice, there have been suggested four main options, as well as variations and combinations thereof:

a) Use of a weak enhancer or a strong enhancer, at a minimal concentration required for extraction completion (non-optimal extractant composition in extraction, high extractant volume, many stages in extraction and relatively high losses). This option was chosen for the citric acid production.

b) Increase the temperature span between extraction and back-extraction (expensive cooling and high viscosity in extraction, and expensive heating and thermal degradation in back-extraction).

c) Distill at least part of the enhancer from the extract prior to back-extraction (high energy cost, limitation to volatile enhancers that in most cases have relatively high solubility in the aqueous streams, requiring additional recovery operations).

d) Add to the extract an a-polar solvent that acts as extraction suppresser, and removal of this solvent prior to the use of the regenerated extractant (low efficiency, high energy cost).

In contradistinction to the above options, a further preferred aspect of the present invention is based on the discovery that polar organic compounds with steric hindrance of the polar group have, at about ambient temperature, an enhancement effect similar to that of similar non-hindered compounds, but lower enhancement effect at elevated temperature. As a result, efficient extraction is achievable using amine-based extractants at about ambient temperature, in combination with convenient amounts of enhancer, while efficient back-extraction is achieved at elevated temperature, without resorting to unduly high temperatures in back-extraction and/or high energy-consuming removal of extractant components, either prior to back-extraction or after it.

In light of the above, there is now provided, according to preferred embodiments of the present invention, a process for the recovery of erythorbic acid from an aqueous feed solution containing values of erythorbic acid at a concentration of less than 0.7 mol/kg, comprising extracting said erythorbic acid with a water-immiscible organic extractant composition comprising (a) at least one secondary or tertiary alkyl amine in which the aggregate number of carbon atoms is at least 20, as a primary extractant, and (b) a sterically hindered, polar, organic, extraction enhancer compound having at least 5 carbon atoms, a basicity weaker than that of said primary extractant, and temperature-sensitive, extraction-enhancing properties; wherein said extractant composition comprises at least 2 moles of said extraction enhancer compound per one mole of primary extractant; separating said erythorbic acid-containing organic extractant composition from residual aqueous solution, and subjecting said erythorbic acid-containing organic extractant composition to a stripping operation with aqueous solution at a temperature of at least 20° C. higher than the temperature at which said extraction is carried out; wherein said extraction enhancer compound both enhances the extracting power of said primary extractant composition and facilitates said temperature-sensitive stripping operation, and whereby there is obtained an aqueous solution of erythorbic acid in which the concentration of erythorbic acid is higher than its concentration in said aqueous feed solution.

In said preferred embodiments of the present invention, said sterically hindered, polar, organic extraction enhancer compound is preferably selected from the group consisting of alkanols, carboxylic acids, tertiary amines, or trialkylphosphates, having a sterically hindering substituent attached to the carbon carrying said polar group, or to a carbon which is alpha, beta, or gamma to said carbon.

Polar, and particularly protic, organic compounds act as enhancers of acid extraction by amines, due to their ability to solvate the amine acid ion pair formed on such extraction. Organic compounds suitable for use as enhancers in the present invention have at least one such polar or protic group, the solvating properties of which are hindered by the structure of the molecule. The polar group is preferably a hydroxyl, an ester, an aldehyde, a carboxyl, a ketone, or an amine, or said polar group can comprise a halogen, sulfur, nitrogen or phosphate atom. The hindrance can be achieved through substitution of a hydrogen atom in the alkyl chain by an aliphatic group, i.e., branching on the carbon atom carrying the polar group, or on a carbon which is alpha, beta, or gamma to said carbon.

The enhancer should be a weaker base than the amine used as the primary extractant in the extractant composite. On equilibrating it with a 0.1M aqueous HCl solution in a proportion that provides for enhancer to HCl molar ratio of 2, the aqueous phase pH will remain below 2. On a similar equilibration, with the amine acting by itself as the non-enhanced extractant, the pH of the aqueous phase increases to about 2.5 or higher.

In addition to the primary extractant and the sterically-hindered, polar, organic enhancer compound, the extractant may comprise a water-immiscible, polar or non-polar solvent, for example, aliphatic or aromatic hydrocarbon, hydrocarbons carrying nitro or halo substituents, and alcohols.

In preferred embodiments of the present invention, said sterically hindered, polar, extraction-enhancing compound is selected from the group consisting of secondary or tertiary alkanols, tris-2-ethylhexyl amine, and tris-2-ethylhexyl phosphate.

The present invention also provides an extractant composition for use in a process for the recovery of erythorbic acid from an aqueous feed solution containing said acid or a salt thereof, said composition comprising (a) at least one secondary or tertiary alkyl amine, in which the aggregate number of carbon atoms is at least 20, as a primary extractant; and (b) a sterically-hindered, polar, organic extraction enhancer compound having at least 5 carbon atoms, a basicity weaker than that of said primary extractant, and temperature-sensitive, extraction-enhancing properties.

In preferred embodiments of the present invention, said extraction composition comprises at least 3 moles of said polar extraction enhancer compound per one mole of primary extractant.

In especially preferred embodiments of the present invention, said stripping action effects the back-extraction of at least 80% of the erythorbic acid contained in said organic extractant composition.

In Japanese 40-2531 there is described a process for the production of a salt of erythorbic acid, which product is separated by crystallization, and thus said patent does not teach or suggest the process of the present invention.

In U.S. Pat. No. 2,160,621 there is described a process for the production of acids related to the erythorbic acid family, which products are separated by crystallization, and thus said patent also does not teach or suggest the process of the present invention.

In U.S. Pat. No. 2,443,487 there is described a process for the production of compounds of the ascorbic acid series using amines as catalysts. The product acid is obtained in the form of an amine salt. It is recovered from this salt by reaction with a base to displace the amine and to form the salt of the acid. In order to recover the product in its acid form, reaction with a mineral acid is required and thus said patent also does not teach or suggest the process of the present invention.

In U.S. Pat. No. 5,041,563 and EP 133,493 an amine is used as a catalyst in the conversion of 2-ketogulonic acid ester to ascorbic acid and the amine salt of the product is formed. The next step is "cleaving the resulting ascorbic acid amine salt by liquid-liquid extraction such that the ascorbic acid is recovered in the polar phase and the amine is recovered in the non-polar phase". One way suggested for doing that, referred to as liquid-liquid extraction, is the addition of water/polar solvent and a non-polar solvent to effect distribution of the acid into the first and the amine to the latter. In certain cases an alternative, referred to as digestion, is heating with a suitable organic solvent, whereby the amine transfers into that solvent and ascorbic acid crystallizes out. Back extraction at a temperature higher than that of extraction is not taught in these publications and thus said references also do not teach or suggest the process of the present invention.

As will be described and exemplified hereinafter, one of the major advantages of the process of the present invention for the recovery of erythorbic acid is that, after said stripping operation, the remaining organic extractant composition can be recycled, and further extraction carried out with said recycled organic extractant composition provides yields of at least 90%, and preferably at least 95%, erythorbic acid.

In most cases at least part of the product is desired in free acid form. In those cases water should be used as said aqueous solution in said stripping operation. When a part of the product is desired in a free acid form and another part of it in a form of a metal ion salt, part of the extracted acid is stripped with water and another part with a solution comprising a base or a salt of said metal ion. In a preferred embodiment a solution comprising a base of the metal ion is used. Preferable the base is selected from a group consisting of hydroxides, bicarbonates, carbonates and mixtures thereof. More preferably said metal ion is an alkali metal ion, most preferably sodium.

It was found that in those cases where a part of the product is desired in a free acid form and another part in a form of a metal ion salt, a preferred combined process involves first stripping erythorbic acid in acid form at the desired proportion by stripping with water and then stripping the rest with a solution comprising a base of the metal ion. Such a combination makes the stripping with water more efficient. Thus, the temperature span between the extraction temperature and that of the stripping could be smaller than in the case where all the extracted acid is stripped with water. Alternatively, the same temperature span is used and the product of stripping with water is more concentrated. In such a preferred embodiment said stripping with a solution comprising a base of the metal ion can be effected at any convenient temperature, which does not need to be higher than that of extraction.

In some cases the aqueous feed solution may consist of erythorbic acid, at least one erythorbate salt or mixtures thereof. The ratio between these constituents is determined by the pH of the solution. For those cases the term "erythorbic acid" would refer to the free acid form of said acid. Thus, in a preferred embodiment, after said stripping operation the remaining organic extraction composition is recycled to extraction. A further extraction carried out with said recycled organic extraction composition preferably provides yields of at least 90%, and more preferably 95% of the ascorbic acid present in said aqueous feed in the free acid form.

In a preferred embodiment of the cases where the aqueous feed solution may consist of erythorbic acid, at least one erythorbate salt or mixtures thereof, erythorbate salts in said aqueous feed may be converted to erythorbic acid prior to said extraction with said water immiscible organic extractant, after such extraction or both. In a preferred embodiment such conversion is effected prior to said extraction and the newly formed erythorbic acid is co-extracted with the acid present there before. In another preferred embodiment the conversion is effected after the extraction and the formed erythorbic acid is recovered by known means, preferably by extraction. More preferably, the extractant used for said recovery of erythorbic acid formed on the conversion of erythorbate salt is of the same composition (in terms of organic components contained), as that used for the extraction of the erythorbic acid content of said aqueous feed. In a further preferred embodiment the extractant used for said recovery of erythorbic acid formed on the conversion of erythorbate salt is the organic extractant composition formed on said stripping operation. In a most preferred embodiment said organic extractant composition formed on said stripping operation is used for the recovery of erythorbic acid formed on the conversion of erythorbate salt and the organic extractant formed is used for the extraction of the erythorbic acid content of said aqueous feed.

Said conversion of erythorbate salt to erythorbic acid is effected by methods known per se. An example for such conversion method is contacting said aqueous solution containing said salt with a water immiscible cation exchanger in its acid form, which cation exchanger could be in solid form, e.g., a resin, or liquid, e.g. a water immiscible organic acid. On such contact cations from said aqueous solution are adsorbed on- or extracted into the said water immiscible cation exchanger and protons are transferred into said aqueous solution forming erythorbic acid therein. In a preferred embodiment of using a liquid cation exchanger, the latter is contacted with said aqueous solution indirectly. An example for such indirect contact is the introduction of a membrane between the liquids. Preferably this membrane is a charged membrane, most preferably a cation exchange membrane.

Preferably said conversion of erythorbate salt to erythorbic acid is effected in a method that does not consume acids and bases as reagents and without rejecting salts into the environment. Such method comprises electrodialytic water splitting using bipolar membranes. In this method electric energy is used as the driving force for said conversion rather than chemical energy. Another method for using electric energy is to use acids and base, e.g. as in the case of conversion through ion exchange, and to decompose the by-product salt formed back into the corresponding acid and base by electrolysis or by electrodialytic water splitting. Other conversion methods suitable for the present invention use $CO_2$ as an acidulant, directly or indirectly.

A preferred embodiment, for those cases where the erythorbic acid formed on said conversion is recovered by extraction, is conducting said extraction simultaneously with said conversion. Such combined conversion and extraction facilitates the conversion. Such combination enables using a water soluble acid as an acidulant, making use of the high selectivity of the extractants used in separating between acids. Thus, an acid less preferred by the extractant than erythorbic acid (HX) is added to the solution consisting of said erythorbate salt. On contact with the extract, erythorbic acid transfers into the extractant and a salt of HX is formed. Alternative, HX is introduced with the extractant.

In those cases where the conversion of erythorbate salts is combined with the extraction of the erythorbic acid formed into a simultaneous operation, and where the composition of the extractant used is as defined for the present invention, said combined operation is considered the step of extracting of erythorbic acid in the invention.

In a preferred embodiment the erythorbic acid and the erythorbate salts, if present, are direct or indirect products of fermentation (i.e. erythorbic acid, erythorbic salts or a mixture thereof is the fermentation product, or is formed by the conversion of a fermentation product). In a further preferred embodiment the aqueous feed solution is a fermentation liquor. Such fermentation liquor is preferably treated prior to the extraction process. Preferably such pretreatment consists of operations such as removal of biomass by methods known per se, e.g. centrifugation, filtration and membrane filtration. If desired, the solution is treated by an adsorbent such as an active carbon, diatomaceous earth or an adsorbing resin. other pretreatments include ion exchange, solvent, extraction, etc.

In another preferred embodiment the aqueous feed is formed in an extractive fermentation. A solution out of the fermentor is contacted with said organic extractant composition to effect said extraction step in which at least a part of the erythorbic acid present therein is extracted and the effluent is recycled to the fermentor, as is or after some treatment. In another preferred embodiment the acid in said solution out of the fermentor is adsorbed on a basic resin or extracted by a basic extractant. The basicity of those could be relatively high, if needed for efficient removal of the erythorbic acid from the solution, which is then recycled to the fermentor, as is or after some treatment. The adsorbed or extracted acid is stripped with a solution of a base to form a solution of an erythorbate salt, which forms the aqueous feed in the present invention, as is or after modification.

The invention will now be described in connection with certain preferred embodiments with reference to the attached figures, so that it may be more fully understood.

With specific reference now to the examples and distribution curves shown in the attached figures in detail, it is stressed that the particulars described and shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to provide details of the invention more than is necessary for a fundamental understanding of the invention, the description taken with the drawings making apparent to those skilled in the art how the several forms of the invention may be embodied in practice.

(Henkel's tricaprylyl amine), 30% octanol (2.4 mole/kg) and 22% kerosene, in equilibrium with aqueous solutions containing 0.15 and 0.3 mole/kg erythorbic acid.

Figure 4:
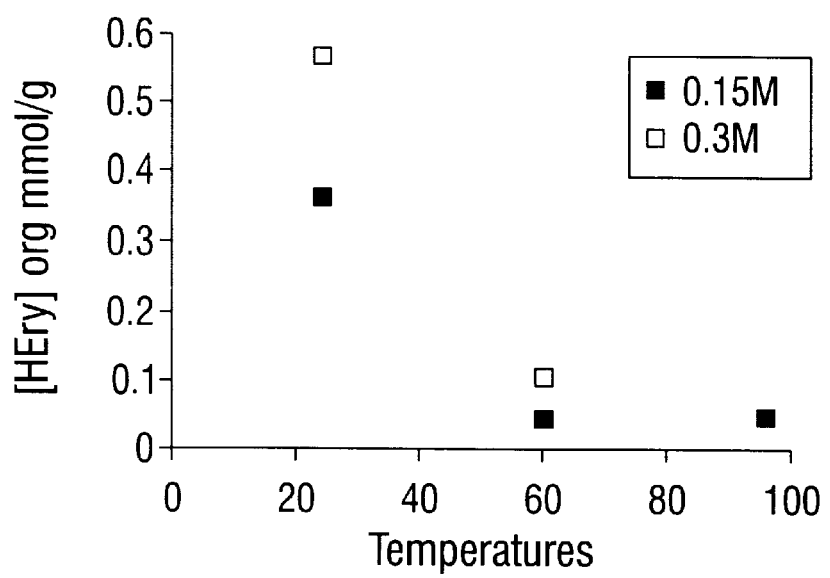

FIG. 4 shows the temperature effect on erythorbic acid extraction by an extractant comprising 48% Alamine 336 (Henkel's tricaprylyl amine), 51% octanol (3.8 mole/kg) and 1% kerosene, in equilibrium with aqueous solutions containing 0.15 and 0.3M erythorbic acid.

Figure 1:
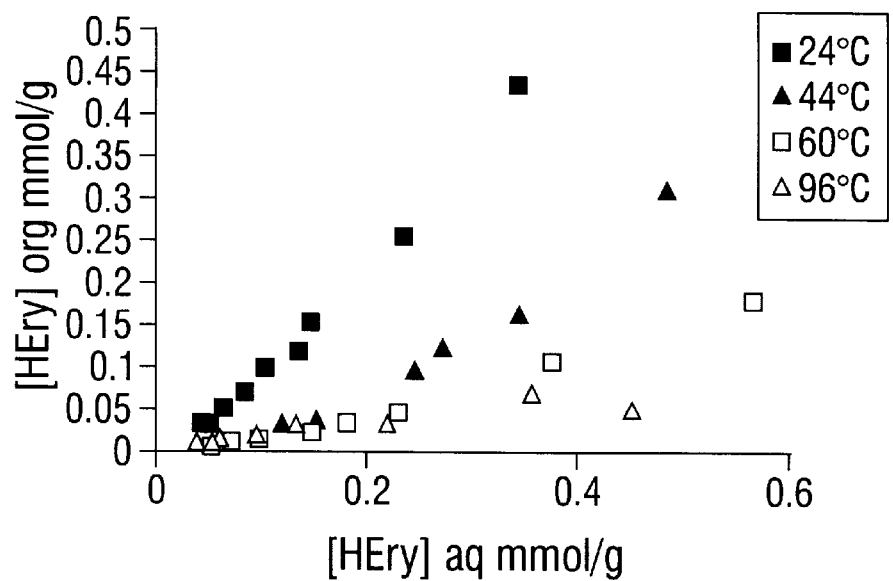
FIG. 1 shows distribution curves for the extraction of erythorbic acid at various temperatures by an extractant comprising 48% Alamine 336 (Henkel's tricaprylyl amine), 30% octanol (2.4 mole/kg) and 22% kerosene.
Figure 3:
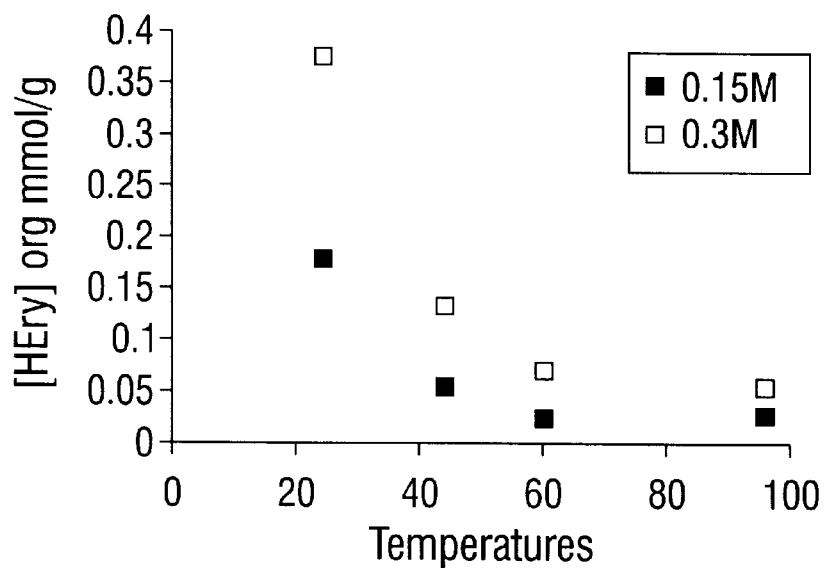
FIG. 3 shows the temperature effect on erythorbic acid extraction by an extractant comprising 48% Alamine 336

FIG. 1 shows distribution curves for the extraction of erythorbic acid at various temperatures by an extractant comprising 48% Alamine 336 (Henkel's tricaprylyl amine), 30% octanol (2.4 mole/kg) and 22% kerosene. Extraction of erythorbic acid at 24° C. from a 0.1 mole/kg solution can reach extractant loading of about 0.1 mole/kg. At 96° C., however, by extrapolating the bottom curve, this extractant loading of 0.1 mole/kg is equivalent to about 0.5 mole/kg erythorbic acid in the aqueous phase. Re-drawing these results in FIG. 3 shows that over the temperature gradient of 24–96° C., the temperature sensitivity factor for erythorbic acid is about 6–7 at the low concentration end. At this extractant composition, the TS for erythorbic acid is higher than those for citric acid and for succinic acid, both of which are about 2–3. Comparison with succinic acid was included herein, in case one were to think that pKa is a factor in the results of the present invention. The pKa of succinic acid is similar to that of erythorbic acid.

The efficiency of extracting erythorbic acid by an extractant containing 2.4 mole/kg octanol is not satisfying and higher enhancer levels are preferred.

Figure 2:
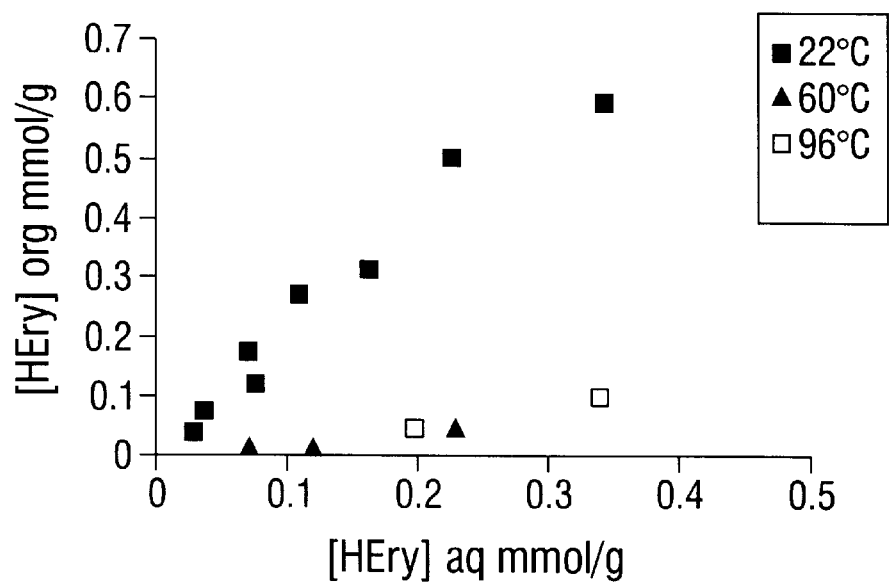
FIG. 2 shows distribution curves for the extraction of erythorbic acid at various temperatures by an extractant comprising 48% Alamine 336 (Henkel's tricaprylyl amine), 51% octanol (3.8 mole/kg) and 1% kerosene.

FIG. 2 illustrates distribution curves for extraction by an extractant composed of 1.2 mol/kg tricaprylyl amine (50%) and 3.8 mol/kg octanol (50%). The loading of the extractant in contact with 0.2 mol/kg erythorbic acid containing aqueous solution is about 0.5 mol/kg. Thus, increasing the content of the enhancer and minimizing the amount of kerosene strongly enhanced the extraction, as compared to that shown in FIG. 1. The effect is even more impressive at the low concentrations end. The effect of the high enhancer level on the temperature sensitivity is surprisingly small. A concentration factor of about 7 can be reached on extraction at 25° C. and back-extraction at 96° C. (see FIG. 4). In comparative distribution curves for the extraction of citric acid by the same extract and practically no temperature sensitivity is found.

Two extractants were tested for the extraction of erythorbic acid. In both, the amine was tricaprylyl amine (Henkel's Alamine 336) and its concentration was 50 w/w %. In one of the extractant compositions, the enhancer was an octanol; in the other extractant composition, it was 3-ethyl-3-pentanol. In both cases, the enhancer content was 50% with no diluent having been used.

Distribution of erythorbic acid between water and these extractants was tested at ambient temperature and at 75° C. The extraction at ambient temperature was similar for both extractants, or even slightly higher in the use of 3-ethyl-3-pentanol. At the elevated temperature, however, the extractant comprising 3-ethyl-3-pentanol was less efficient.

From these results, it can be realized that using a sterically hindered polar organic compound having at least 5 carbon atoms, a basicity weaker than that of the primary extractant, and temperature-sensitive, extraction-modifying properties as the extraction enhancer compound of the present invention, is indeed preferred.

Referring once again to the teachings of U.S. Pat. No. 4,275,234, it will be noted that several difficulties are indicated in the examples of said patent:

In most examples, no enhancer was used in the extractant, or it is used in a limited proportion of up to 5%. In Example 7, the extractant composition is 50% tri-tridecylamine and 50% nitrobenzene. Being a polar component, nitrobenzene is quite efficient as an enhancer. An extract containing 9.3% citric acid was back-extracted with water (100 g per 100 g of extract) at 60° C. (35° C. higher than the extraction temperature). Only 13% of the initial citric acid was back-extracted, forming a dilute solution of 13% citric acid. Adding 150 g hydrocarbon to dilute the amine and the enhancer was needed to improve the back-extraction. This example concluded that "the extract could not readily be back-extracted unless a hydrocarbon fraction was added to it." Addition of the hydrocarbon at the extraction step would have reduced its efficiency, as non-polar solvents act contrary to the enhancers and could be referred to as extraction inhibitors.

Example 16 of said patent describes the back-extraction of oxalic acid from an extractant composed of 25% w/w dilaurylbenzyl amine, 69% w/w n-octane and 6% 1-n-octanol. For efficient back-extraction, 50 g of n-octane were added to about 37 g of oxalic acid-containing extract. Thus, even at relatively low initial enhancer levels, substantial dilution by an extractant inhibitor was required. Only about 79% of the extracted acid is back-extracted at 80° C. Temperatures of 120–160° C. are recommended (Example 18).

The yield of lactic acid recovery from an initial solution comprising 1.1 mol/kg acid was 95% (Example 13). Enhancer-free extractant was used. The yield for $H_3PO_4$ recovery from an initial solution of 0.8 mol/kg was 88% (Example 14). Here again, no enhancer was used. The extraction yield for citric acid in Example 5 was 95%, using an extractant comprising 5% enhancer (octanol).

In said patent, there also appears in Example 12 a description of the extraction of dilute lactic acid in which high amounts of enhancer are ostensibly used with good results. According to the principles and theory of the present invention, the results obtained in Example 12 of U.S. Pat. No. 4,275,234 did not appear to be possible or correct. In order to clarify this point, the extraction of lactic acid from a 2% (0.22 mol/kg) solution and its stripping from the extractant were repeated as in Example 12. The extractant was composed of 50% w/w tridodecylamine and 50% w/w of 1-n-octanol. The extraction was conducted at 25° C. and the stripping at about 96° C.

Extraction as in Example 12 (100 g aqueous, 40 g extractant, 3 counter-current stages) results in practically complete extraction of the acid to form an extract (loaded extractant) comprising 5% w/w lactic acid. Stripping as in Example 12 (40 g extract, 40 g water, 5 counter-current stages) results in an aqueous solution comprising 0.7 g lactic acid in concentration of 1.8%. About two-thirds of the extracted lactic acid stays in the organic phase. Re-use of this organic phase in extraction from 2% lactic acid solutions results in low yields; not more than 20% of the acid is extracted. Increasing the number of stages in extraction has only a small effect. Near complete stripping and thus high yield in re-use of the organic phase requires about 150 g water per 40 g of extract, and 6–7 counter-current stages. The lactic acid in this case is obtained in a dilute solution of about 0.5% w/w.

Thus, using an extractant comprising about 4 moles of enhancer per mole amine provides for nearly complete extraction of lactic acid from a dilute solution of 0.22 mol/kg, but on stripping, a high proportion of water is required and the acid is diluted 4 times, compared to its concentration in the feed. The cost of concentrating this solution is enormous.

Using the same extractant for extracting erythorbic acid from 0.22 mol/kg solution, 65 g of extractant per 100 g aqueous solution and 5–6 counter-current stages, are required to reach an extraction yield of at least 95% at 25° C.

Stripping the extract at 96° C. with 35 g water results in an aqueous solution comprising 0.6 mol/kg erythorbic acid and an organic phase practically free of erythorbic acid. Re-use of this organic phase in extraction provides an extraction yield of at least 95% at the above conditions.

Thus, while in the case of lactic acid, practically complete extraction with recycled extractant results in a lactic acid product diluted 4 times compared with the feed, in the case of erythorbic acid at the same conditions and with similar extractant, practically complete extraction with recycled extractant results in erythorbic acid product solution concentrated 3 times compared with the feed.

Therefore, it is clear that one following the teachings of U.S. Pat. No. 4,275,234 and repeating the examples contained therein would come to the inescapable conclusion that the process taught therein is not suitable for the commercial production of erythorbic acid. Furthermore, said patent certainly does not teach or suggest the use of a sterically-hindered, polar, organic, extraction enhancer compound as described and claimed herein.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for the recovery of erythorbic acid from an aqueous feed solution containing values of erythorbic acid at a concentration of less than 0.7 mol/kg, comprising:
    extracting said erythorbic acid with a water-immiscible organic extractant composition comprising (a) at least one secondary or tertiary alkyl amine in which the aggregate number of carbon atoms is at least 20, as a primary extractant, and (b) a polar extraction enhancer compound; wherein said extractant composition comprises at least 2 moles of said polar extraction enhancer compound per one mole of primary extractant;
    separating said erythorbic acid-containing organic extractant composition from residual aqueous solution, and
    subjecting said erythorbic acid-containing organic extractant composition to a stripping operation with aqueous solution at a temperature of at least 20° C. higher than the temperature at which said extraction is carried out;
    whereby there is obtained an aqueous solution of erythorbic acid in which the concentration of erythorbic acid is higher than its concentration in said aqueous feed solution.

2. A process for the recovery of erythorbic acid as claimed in claim 1, wherein said extractant composition comprises at least 3 moles of said extraction enhancer compound per one mole of primary extractant.

3. A process for the recovery of erythorbic acid as claimed in claim 1, wherein said stripping action effects the back-extraction of at least 80% of the erythorbic acid contained in said organic extractant composition.

4. A process for the recovery of erythorbic acid as claimed in claim 1, wherein, after said stripping operation, the remaining organic extractant composition is recycled.

5. A process for the recovery of erythorbic acid as claimed in claim 4, wherein further extraction carried out with said recycled organic extractant composition provides yields of at least 90% erythorbic acid.

6. A process for the recovery of erythorbic acid as claimed in claim 4, wherein further extraction carried out with said recycled organic extractant composition provides yields of at least 95% erythorbic acid.

7. A process for the recovery of erythorbic acid as claimed in claim 1, wherein said aqueous feed solution contains said acid at a concentration of less than 0.5 mol/kg.

8. A process according to claim 1, for the recovery of erythorbic acid from an aqueous feed solution containing values of erythorbic acid at a concentration of less than 0.7 mol/kg, comprising extracting said erythorbic acid with a water-immiscible organic extractant composition comprising:
    (a) at least one secondary or tertiary alkyl amine in which the aggregate number of carbon atoms is at least 20, as a primary extractant, and
    (b) a sterically hindered, polar, organic, extraction enhancer compound having at least 5 carbon atoms, a basicity weaker than that of said primary extractant, and temperature-sensitive, extraction-enhancing properties;
    wherein said extractant composition comprises at least 2 moles of said extraction enhancer compound per one mole of primary extractant;
    separating said erythorbic acid-containing organic extractant composition from residual aqueous solution, and
    subjecting said erythorbic acid-containing organic extractant composition to a stripping operation with aqueous solution at a temperature of at least 20° C. higher than the temperature at which said extraction is carried out;
    wherein said extraction enhancer compound both enhances the extracting power of said primary extractant composition and facilitates said temperature-sensitive stripping operation, and
    whereby there is obtained an aqueous solution of erythorbic acid in which the concentration of erythorbic acid is higher than its concentration in said aqueous feed solution.

9. A process according to claim 8, wherein said sterically hindered, polar, organic, extraction enhancer compound is selected from the group consisting of alkanols, carboxylic acids, tertiary amines, and trialkylphosphates having a sterically hindering substituent attached to the carbon carrying said polar group, or to a carbon which is alpha, beta, or gamma to said carbon.

10. A process according to claim 9, wherein said substituent is an aliphatic group.

11. A process according to claim 8, wherein said extraction enhancer compound is selected from the group consisting of secondary or tertiary alkanols, tris-2-ethylhexyl amine, and tris-2-ethylhexyl phosphate.

12. A process according to claim 1, wherein the aqueous feed solution containing values of erythorbic acid is obtained by fermentation.

13. A process for the recovery of erythorbic acid as claimed in claim 1, wherein water is used as said aqueous solution in said stripping operation.

14. A process for the recovery or erythorbic acid as claimed in claim 1, wherein erythorbic acid left in said organic extractant after said stripping operation is stripped with an aqueous solution of a base.

15. A process for the recovery of erythorbic acid as claimed in claim 14, wherein said base is selected from a group consisting of alkali metal hydroxides, bicarbonates and carbonates.

16. A process for the recovery of erythorbic acid as claimed in claim 1, wherein said aqueous feed solution consists of erythorbic acid, at least one erythorbate salt or mixtures thereof.

17. A process for the recovery of erythorbic acid as claimed in claim 16, wherein erythorbate salts in said aqueous feed are converted to erythorbic acid prior to said extraction with said water immiscible organic extractant.

18. A process for the recovery of erythorbic acid as claimed in claim 16, wherein erythorbate salts in said aqueous feed are converted to erythorbic acid after said extraction with said water immiscible organic extractant.

19. A process for the recovery of erythorbic acid as claimed in claim 16, wherein erythorbate salts in said aqueous feed are converted to erythorbic acid simultaneously with said extraction with said water immiscible organic extractant.

20. A process for the recovery of erythorbic acid as claimed in claim 17, wherein said conversion is conducted by a method selected from a group consisting of methods utilizing ion exchangers, extraction, $CO_2$ as an acidulant, charged membranes, electric energy and combinations thereof.

21. A process for the recovery of erythorbic acid as claimed in claim 18, wherein said conversion is conducted by a method selected from a group consisting of methods utilizing ion exchangers, extraction, $CO_2$ as an acidulant, charged membranes, electric energy and combinations thereof.

22. A process for the recovery of erythorbic acid as claimed in claim 17, wherein said conversion is conducted by a method selected from a group consisting of methods utilizing ion exchangers, extraction, $CO_2$ as an acidulant, charged membranes, electric energy and combinations thereof.

23. A process for the recovery of erythorbic acid as claimed in claim 1, wherein said aqueous feed solution is a fermentation liquor.

24. A process for the recovery of erythorbic acid as claimed in claim 23, wherein said aqueous feed solution is continuously extracted during fermentation in a continuous fermentation process.

25. A process for the recovery of erythorbic acid as claimed in claim 23, wherein said fermentation liquor is pretreated prior to said extraction step.

26. A process for the recovery of erythorbic acid as claimed in claim 25, wherein said pretreatment is an operation selected from a group consisting of biomass removal and treatment with an adsorbent, ion exchanger and a solvent or mixtures thereof.

27. A process for the recovery of erythorbic acid as claimed in claim 26, wherein said biomass removal is effected by membrane filtration.

\* \* \* \* \*